[12] United States Patent  
Legay et al.

(10) Patent No.: US 11,097,119 B2  
(45) Date of Patent: *Aug. 24, 2021

(54) SYSTEM AND METHOD FOR PROTECTING AGAINST MAGNETIC FIELDS PRODUCED BY MRI

(71) Applicant: SORIN CRM SAS, Clamart (FR)

(72) Inventors: Thierry Legay, Fontenay les Briis (FR); Dominique Decoene, Jouars Pontchartrain (FR)

(73) Assignee: Sorin CRM SAS, Clamart (FR)

( * ) Notice: Subject to any disclaimer, the term of this patent is extended or adjusted under 35 U.S.C. 154(b) by 130 days.

This patent is subject to a terminal disclaimer.

(21) Appl. No.: 16/192,984

(22) Filed: Nov. 16, 2018

(65) Prior Publication Data

US 2019/0083802 A1 Mar. 21, 2019

Related U.S. Application Data

(63) Continuation of application No. 13/009,629, filed on Jan. 19, 2011, now Pat. No. 10,130,822.

(30) Foreign Application Priority Data

Jan. 20, 2010 (FR) ...................................... 1050374

(51) Int. Cl.
*A61N 1/39* (2006.01)
*A61N 1/37* (2006.01)
*A61B 5/055* (2006.01)

(52) U.S. Cl.
CPC ......... *A61N 1/3925* (2013.01); *A61N 1/3718* (2013.01); *A61B 5/055* (2013.01)

(58) Field of Classification Search
CPC ..... A61N 1/3925; A61N 1/3718; A61B 5/055
See application file for complete search history.

(56) References Cited

U.S. PATENT DOCUMENTS

| | | | |
|---|---|---|---|
| 6,937,906 | B2 | 8/2005 | Terry et al. |
| 7,082,328 | B2 | 7/2006 | Funke |
| 7,174,202 | B2 | 2/2007 | Bladen et al. |
| 7,561,915 | B1 | 7/2009 | Cooke et al. |
| 7,719,280 | B2 | 5/2010 | Lagae et al. |
| 2002/0138124 | A1 | 9/2002 | Helfer et al. |

(Continued)

*Primary Examiner* — Allen Porter
*Assistant Examiner* — James Moss
(74) *Attorney, Agent, or Firm* — Foley & Lardner LLP

(57) ABSTRACT

An implantable cardiac device that detects and protects against strong magnetic fields produced by MRI equipment is disclosed. The device has a magnetic field sensor for detecting the presence of a relatively weak static magnetic field (102, 110, 118, 122) of a level equivalent to that of a permanent magnet in the vicinity of the device. The device is switched from a standard operating mode (100) where the nominal functions of the device are active, to a specific protected MRI mode (114, 116) in the presence of a magnetic static field of a level corresponding to that emitted by MRI equipment. The device further temporarily switches the device from the standard operating mode (100) to an MRI stand-by state (108) when a magnetic field is detected by the magnetic field sensor such that a subsequent detection of a magnetic field switches the device from an MRI stand-by state to the specific protected MRI mode.

18 Claims, 1 Drawing Sheet

(56) References Cited

U.S. PATENT DOCUMENTS

| | | | |
|---|---|---|---|
| 2003/0114897 A1* | 6/2003 | Von Arx | A61N 1/37276 607/60 |
| 2004/0010292 A1* | 1/2004 | Amblard | A61N 1/368 607/9 |
| 2005/0240235 A1* | 10/2005 | Limousin | A61N 1/365 607/9 |
| 2006/0036126 A1 | 2/2006 | Ross et al. | |
| 2006/0173295 A1 | 8/2006 | Zeijlemaker | |
| 2007/0173890 A1* | 7/2007 | Armstrong | A61N 1/37252 607/2 |
| 2008/0147135 A1 | 6/2008 | Hareland | |
| 2009/0138058 A1* | 5/2009 | Cooke | A61N 1/36092 607/5 |
| 2009/0157146 A1* | 6/2009 | Linder | A61N 1/37217 607/60 |
| 2009/0163980 A1 | 6/2009 | Stevenson | |
| 2010/0016914 A1* | 1/2010 | Mullen | A61N 1/36843 607/14 |
| 2011/0077706 A1* | 3/2011 | Ellingson | A61N 1/3718 607/17 |
| 2011/0106212 A1* | 5/2011 | Ellingson | A61N 1/3718 607/59 |
| 2011/0106218 A1* | 5/2011 | Stancer | A61N 1/3754 607/63 |

* cited by examiner

SYSTEM AND METHOD FOR PROTECTING AGAINST MAGNETIC FIELDS PRODUCED BY MRI

CROSS-REFERENCE TO RELATED APPLICATIONS

This application is a Continuation of U.S. patent application Ser. No. 13/009,629, filed Jan. 19, 2011, which claims the benefit of French Application No. 1050374, filed Jan. 20, 2010, both of which are hereby incorporated by reference in their entirety.

FIELD

The present invention relates to "active implantable medical devices" as defined by Directive 90/385/EEC of 20 Jun. 1990 of Council of European Communities, and more particularly to devices that continuously monitor heart rhythm and if necessary deliver to the heart of a patient resynchronization and/or defibrillation electrical stimulation pulses, in cases of arrhythmias detected by the device.

The present invention relates even more particularly to techniques for protecting these devices (e.g., generators and their associated sensors) when the patient is subject to an examination by magnetic resonance imaging (MRI) equipment.

BACKGROUND

Active implantable medical devices include a housing containing various electronic circuits and a battery, generally referred to as a generator, that is electrically and mechanically connected to one or more leads with electrodes. The leads are intended to come into contact with a tissue of the patient, e.g., the myocardium, at sites where electrical potentials can be collected (i.e., detected) and/or stimulation pulses can be applied (i.e., delivered).

MRI examination has been contraindicated for patients with an implanted cardiac pacemaker or defibrillator type of generator. Several types of problems arise under this situation:

heating near the electrodes connecting the generator to the patient's heart;

forces and torques of attraction exerted on the device immersed in the high intensity static magnetic field produced by the MRI equipment during an examination; and unpredictable behavior of the device itself due to the exposure to the strong magnetic field.

It is an objective of the present invention to provide a solution to the above described problems, particularly to avoid malfunction or unpredictable behavior of the device in a strong magnetic field. In this regard, it is desirable that when the device is exposed to (static and alternating) electromagnetic fields generated by MRI equipment, the behavior of the device is documented and known in advance.

In the absence of special precautions, the problems that are likely to affect the behavior of the device under an MRI examination include an erratic detection of strong static field generated by MRI equipment, especially in devices equipped with a Reed magnetic switch. A Reed magnetic switch is used to detect and respond to the presence of a permanent magnet in the vicinity of the device. A permanent magnet is normally used by a practitioner to put the device in a safe operating or "magnet" mode, for example, when using an electric scalpel, or evaluating battery depletion of the device. In a magnet mode, the stimulation frequency is generally fixed and reflects the level of battery charge. A Reed magnetic switch is designed to detect static magnetic fields of relatively low intensity, but is likely to exhibit a totally unpredictable behavior in an MRI examination environment where the magnetic fields are often thousands of times stronger than that of a permanent magnet. Problems also may include deterioration of the intrinsic performance of the device, and misinterpretation of the dynamic signals emitted by the MRI equipment by the device as cardiac signals, including, for example, an inhibition of the stimulation function by the dynamic signals emitted by the MRI equipment that are inadvertently detected by the device as cardiac signals.

Throughout the duration of an MRI examination—which can last several minutes—the device should nevertheless remain functional and provide if necessary seamless and predictable stimulation to the patient's myocardium. It is therefore desirable to have means for detecting and means for managing such a situation, providing the following functions:

indicating to the device that the patient will be subjected to an MRI examination;

inhibiting the circuits of the device that may be disturbed by the electromagnetic fields emitted by the MRI equipment; and operating the device in a dedicated pacing mode, tailored to the patient and compatible with the electromagnetic fields emitted by the MRI equipment.

Special techniques have been proposed to detect static magnetic fields of an MRI type, with strength in the order of Tesla (typically between 0.5 and 3 T, and herein referred to as a "strong magnetic field"): In the majority of the devices that are sensitive to the presence of a permanent magnet are those devices that have a magnetic field detector that detects weak magnetic fields (e.g., a static magnetic field in the order of 1.5 mT; and herein referred to as a "weak magnetic field"), but is unable to detect the strong magnetic fields that are produced by MRI equipment. Because the magnetic fields produced by MRI equipment are up to thousands of times stronger than that produced by a permanent magnet, and are in the non linear response zone of these weak magnetic field detectors, it poses a risk that the weak magnetic field detectors will be "deaf" to the presence of a strong magnetic field.

The U.S. Patent Publication US 2007/191914 A1 describes a device in which the presence of a strong static magnetic field is detected by an analysis of the impedance of an inductive component, e.g., one of the coils of an inductive switching regulator. The presence of a strong magnetic field has the effect of saturating the core of this inductive component, causing an impedance change that can be reported to the device.

WO 2006/124481 A2 discloses another technique for detecting the presence of an MRI-type magnetic field by the measurement of the voltage sensed across a telemetry antenna and on the lead.

EP 1935450A1 describes yet another technique of using giant magnetoresistance (GMR) sensors associated within a Wheatstone bridge. The Wheatstone bridge acts as a single mixed strong I weak field sensor. The balance of the Wheatstone bridge is more or less altered by a magnetic field, and the resulting changes from the differential voltage can be analyzed by a converter placed at the output of the bridge to give an overall estimate of the field strength.

The U.S. Patent Publication US2009/0138058 A1 provides a programming technique to place the device in a state of waiting for MRI (referred to as an MRI mode), for example, during a consultation with a cardiologist. In this state of waiting, the device operates in its standard mode of operation, but with an expectation of detecting a strong static magnetic field. In the presence of a strong magnetic field (e.g., at the beginning of an MRI examination), the device then switches to an MRI-safe mode that is compatible with a strong magnetic field for the duration of the MRI examination. Once the MRI examination is completed, the device is reset to a normal mode of operation (referred to as a normal operation mode).

Some of these various techniques detect a strong magnetic field using an additional sensor (i.e., not the sensor responsive to a weak magnetic field). If these devices do not contain a strong magnetic field sensor, it is required to redesign the hardware of the device, incurring an additional cost and creating an extra constraint on the circuits against the design requirements for miniaturizing these devices.

OBJECT AND SUMMARY

It is, therefore, an object of the present invention is to provide a new technique particularly applicable to conventional and/or older generation devices, with no dedicated sensor for detecting a strong magnetic field generated by MRI equipment, to protect such devices during an examination by the MRI equipment.

It will be seen in particular that the technique of the present invention can be implemented by a simple software adaptation to an existing microcontroller of an active implantable medical device without having to modify the hardware design, and thus provides a large economy of savings in connection with implementing the invention with no significant extra cost.

The basic principle of the present invention is to use a magnetic field sensor that is present in the device for detecting a weak magnetic field (typically a low static magnetic field in the order of millitesla, mT), such as is generated by a permanent magnet used to place the device in a "magnet mode". The magnetic field sensor is used without hardware changes to the device for placing the device in a state of waiting for MRI (also referred to as "stand-by state"), for example, during a cardiac consultation.

When a patient undergoes an MRI examination, an appointment is given by a radiology center. Prior to the appointment, the patient meets with his or her cardiologist, who places the device in a stand-by state for an MRI examination.

In a stand-by state for MRI, the operation of the device is initially in a standard operation mode, until the occurrence of a trigger events such as one of the following two events:
(1) when the patient enters the examination room where MRI equipment is located, the device detects a relatively high static magnetic field: although significantly weaker than the strong magnetic field that will be generated by the MRI equipment during the actual examination, such a relatively higher static field is present in the examination room even when no test is in progress; and
(2) just before the entrance of the patient in the room of the MRI equipment, a permanent magnet is applied by an operator to the patient's chest in the vicinity of the device.

Either of these two events thus places the device in a specific mode of operation, modified from the standard operation mode that is compatible with a strong magnetic field during the MRI examination. It is noted that the transition to the specific mode of operation is made just before the beginning of the MRI examination, either automatically upon entering the examination room or by a special programming (e.g., application of a permanent magnet).

Once the MRI examination is completed and the level of ambient magnetic field has dropped to a lower level, e.g., when the patient has left the examination room, the device automatically detects the change in the magnetic field level and returns to its normal operation mode, without any necessary intervention such as by reprogramming the device as described in US2009/0138058 A 1.

In one embodiment, when the device is switched to the MRI stand-by state, the cardiologist may program a timer with a predetermined period (e.g., a few hours, several weeks). When the timer is activated by such programming, the device is put in the MRI stand-by state. After the predetermined period, for safety purpose, the device automatically exits the MRI stand-by state without the need of any additional consultation of the cardiologist.

One embodiment of the present invention is directed to a device of the type disclosed in US2009/0138058A1 that comprises: a generator containing an electronic circuit of detection/stimulation; means for switching the device from a standard operating mode where nominal functions of the device are active to a specific protected MRI mode in the presence of a strong magnetic field of a level equivalent to the static magnetic field emitted by MRI equipment; emitting/receiving telemetry for ensuring a coupling of the device with an external programmer device; and means for temporarily setting the device in an MRI stand-by state.

Characteristically of the present invention, the device includes a magnetic field sensor detecting the presence of a weak static magnetic field equivalent to that emitted by a permanent magnet in the vicinity of the device. Moreover, the device is returned from the specific protected MRI mode back to the standard operating mode, in the absence of that weak magnetic field being sensed by the magnetic field sensor.

Advantageously, the means for switching to place the device in the MRI stand-by state is activated upon detecting a magnetic field (e.g., entrance to the MRI examination room, application of a permanent magnet in the vicinity of the device) by the magnetic field sensor. The means for switching may be alternatively activated via transmitter/receiver telemetry means.

Further, means for repositioning may be provided to return the device from operating in the MRI stand-by state or the specific protected MRI mode back to the operating standard mode. Such a means for repositioning may be activated via the transmitter/receiver telemetry means.

According to one embodiment, the device further comprises a timer for counting a predetermined time from the moment the device is placed in the MRI standby state, and means for automatically placing the device in the standard operating mode at the expiry of the timer. The predetermined time may be programmable data by an external programmer and transmitted to the device via the transmitter I receiver telemetry means.

Preferably, the device further comprises means for inhibiting the switch back of the device from the specific protected MRI mode to the standard operating mode, the means for inhibiting operating during a predetermined period counted from the moment of the switching in the specific protected MRI mode. This timing may be a predetermined time period programmed by the external programmer device and transmitted to the device via the transmitter/receiver telemetry means.

The magnetic field sensor is typically a weak magnetic field sensor adequate for detecting the presence of a static magnetic field of a level of at least 1 mT. In one embodiment, it is selected from the group consisting of: a coil whose core tends to saturate in the presence a weak magnetic field, a giant magnetoresistance GMR sensor, a Hall effect sensor, an integrated MAGFET sensor, and a MEMS sensor.

The means for switching includes, when activated, means for putting the device into a specific mode that is protected against MRI, such as a magnet mode without detection; means for inhibiting the elements of the device sensitive to the deleterious effects when exposed to static and alternating radiofrequency magnetic fields emitted by MRI equipment; and means for generating pacing pulses at a predetermined frequency, independent of the battery level of the power supply of the device.

BRIEF DESCRIPTION OF THE DRAWINGS

Further features, characteristics and advantages of the present invention will become apparent to a person of ordinary skill in the art from the following detailed description of various embodiments of the present subject matter made with reference to the annexed drawings, in which.

DETAILED DESCRIPTION

Figures 1, 2:
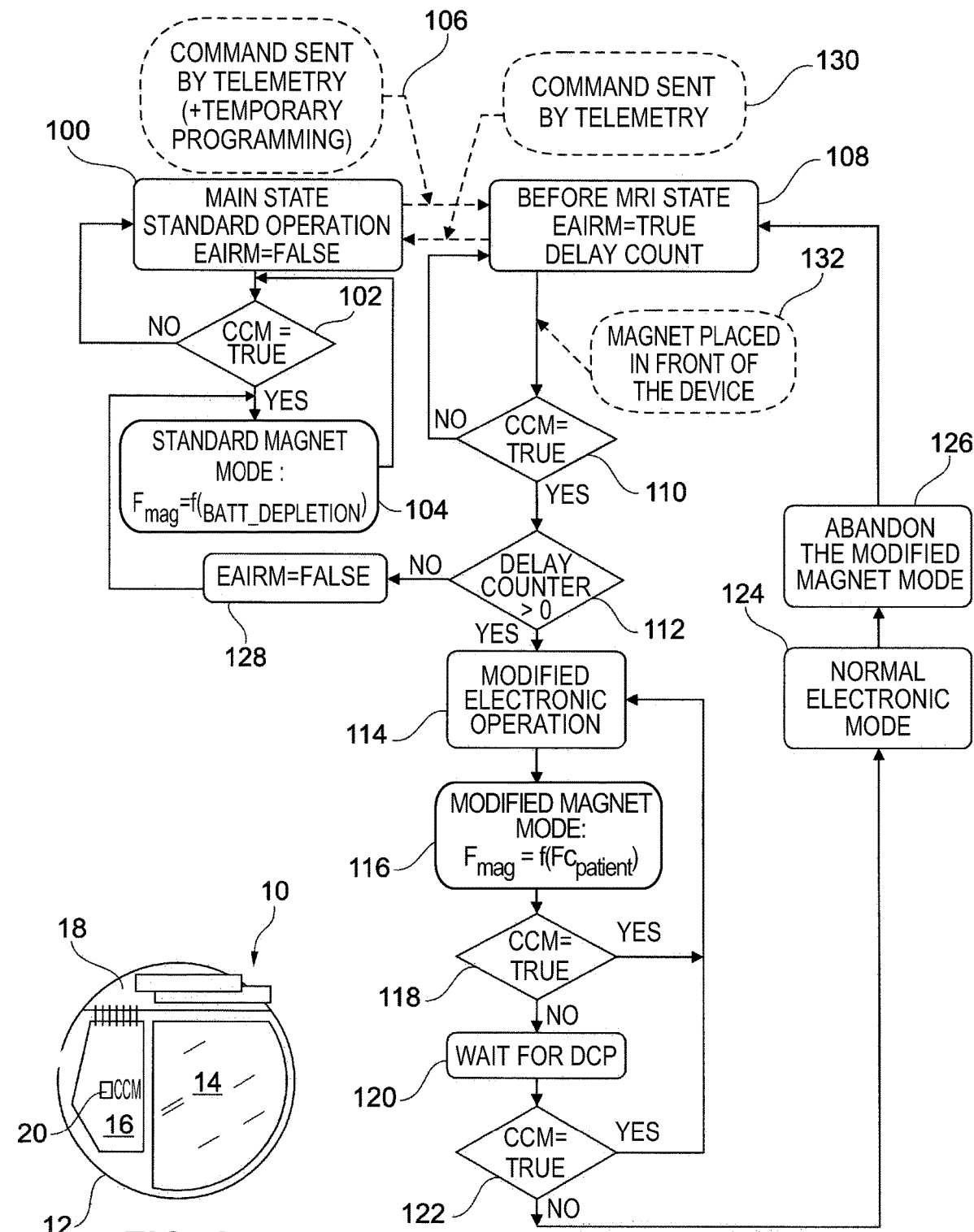
FIG. 1 is a schematic view of an implantable medical device, according to a preferred embodiment of the invention.
FIG. 2 is a diagram of the operation of the device of FIG. 1, according to one embodiment of the present invention.

The present invention may be implemented by an appropriate programming of the controlling software of a known device of, for example, a cardiac pacemaker, resynchronizer and/or defibrillator type, including means for acquiring a signal provided by endocardial leads and/or one or more implanted sensors. The adaptation of these devices to implement the functions of the present invention is believed to be within the abilities of a person of ordinary skill in the art, and therefore will not be described in detail.

The present invention may particularly be applied to implantable devices such as those of the Reply and Paradym families produced and marketed by Sorin CRM, Clamart, France. These devices include programmable microcontroller and microprocessor circuitry to receive, format, and process electrical signals collected by implanted electrodes and deliver pacing pulses to these electrodes. It is possible to transmit by telemetry software and to store the software in the memory and execute the software to implement the functions of the present invention as described herein.

With reference to FIG. 1, the housing 12 of an implantable medical device 10 contains a battery 14 and an electronic circuit 16. The electronic circuit 16 is connected to a connector 18 that removably receives one or more leads (not shown) having electrodes for detection and/or stimulation.

The device 10 is also equipped with a magnetic field sensor 20 for detecting a weak static magnetic field, typically in the order of millitesla (mT).

The commonly used techniques for detecting a permanent magnet place the device 10 in a specific "magnet mode". The sensor 20 may be chosen from among the group comprising: a coil whose core saturates in the presence of a weak magnetic field, a giant magnetoresistance (GMR) sensor, a Hall effect sensor, an integrated MAGFET component, (as described by example in WO 94/12238A1), or a micro electromechanical system (MEMS) sensor (as described, for example, in FR 2805999 A 1). A Reed magnet switch that contains metal elements is preferably avoided because of its generally unpredictable and unreliable behavior in the presence of strong magnetic fields.

The sensor 20 contained in the device 10 advantageously allows for implementing the present invention without any hardware changes to the device 10, and for retrofitting already implanted devices. The sensor 20 outputs a binary 'true' or 'false' CCM signal, depending on whether a magnetic field stronger than a threshold level is detected. The threshold level is typically greater than or equal to 1 mT.

FIG. 2 is a flowchart explaining a detailed implementation of the technique according to the present invention.

In the initial state (block 100), the device 10 is in a standard (unmodified) operation mode. A binary indicator EAIRM (corresponding to the MRI stand-by state) is set to 'false'.

According to one embodiment, upon detecting a magnetic field (CCM='true' in test 102) by the sensor 20, the device 10 goes into a "magnet mode" (block 104). In the magnet mode (also referred to as a 'standard magnet mode'), the patient is paced in a conventional 000 mode with a stimulation frequency that is determined based on the level of battery depletion (which allows testing of that level). Other conventional asynchronous pacing modes can be used as deemed appropriate for the device used and the patient, e.g., VOO, AOO.

When the magnetic field is removed (CCM='false' in test 102), the device 10 returns to the programmed standard mode of operation. The operation in a standard mode, which may actually comprise a number of different standard operating modes responsive to the patient's condition, is well known in the art.

According to another embodiment, in the standard mode (block 100), the device 10 receives a command 106 via telemetry (telemetry or inductive telemetry RF), e.g., on the orders of a cardiologist. The command 106 switches the device 10 to the MRI stand-by state (block 108).

The MRI stand-by state is maintained while the patient undergoes an MRI examination during a period of time, typically between a few minutes and a few hours. The MRI stand-by state may be extended to a few days to weeks as the cardiologist determines appropriate. The EAIRM indicator is set to 'true', and the MRI stand-by state time is programmed by the cardiologist, up to the maximum allowable time that the device 10 can remain in the MRI stand-by state. A countdown timer starts immediately after the device 10 switches to the MRI stand-by state. Alternatively, the countdown timer may be deferred for another programmable period before the device 10 switches to the MRI stand-by state.

In the MRI stand-by state, the device 10 operates with all the usual features, for example, in the same standard operating mode of the main block 100.

The standard operating mode is maintained until the magnetic field sensor 20 detects a static field (test 110, CCM='false'). If, however, (i) the sensor 20 detects the presence of a magnetic field (test 110, CCM='true') and (ii) the countdown timer has not expired (test 112), the device 10 considers that the patient will be subjected soon to a strong magnetic field.

The device 10 changes its electronic behavior (block 114) by turning off a number of circuits directly or indirectly, especially the RF telemetry circuits and the switching converters for power supply. The power systems are based on linear voltage regulators or capacitive converters, consuming more energy, but insensitive to the effects of magnetic fields.

After changing its electronic behavior, the device 10 changes its operating mode (block 116) to a 'modified magnet mode' in which:

the pacing frequency is no longer based on the battery depletion (as in the 'standard magnet mode'), for example, on the average of the patient's heart rhythm;

the detection function is inhibited to avoid misinterpretation of the dynamic signals emitted by the MRI equipment as cardiac signals; and in the case of an implantable defibrillator, any delivery of shocks is inhibited.

The 'modified magnet mode' (also referred to herein as a specific protected MRI mode) is maintained during the MRI examination.

The test for detecting the magnetic field is repeated (test 118). If the test is positive (i.e., CCM='true'), the device 10 maintains the modified magnet mode. Otherwise the test is negative (i.e., CCM='false'), and the device 10 waits for the expiration of a programmable confirmation time (DCP), for example, 10 minutes (block 120), after which the test for the presence of the magnetic field is repeated (test 122). If this test is positive (i.e., CCM='true'), the device 10 remains in the current modified magnet mode; otherwise (i.e., CCM='false'), the device 10 switches to the standard electronic operation (block 124) restoring the altered functions in block 114, and the modified magnet mode is abandoned (block 126) restoring the altered functions in block 116. The functions and the mode of operations that prevailed before detecting a magnetic field during test 110 are returned to the MRI stand-by state with standard operation of block 108.

When the device 10 is in the MRI stand-by state (block (108)), if (i) the sensor detects the presence of a magnetic field (test 110, CCM='true') but (ii) the timer is expired (test 112), the MRI stand-by state is cancelled (block 128, EAIRM indicator set to 'false'). The device 10 reverts to the 'standard magnet mode' (block 104), and the test 102 for testing the presence of the field is repeated. If this test 102 is negative (CCM='false'), the device 10 returns to the standard mode corresponding to the initial state of operation (block 100) prior to the activation of the MRI stand-by mode by the cardiologist.

In another embodiment, the device 10 is forced to return to the standard state by a telemetry instruction 130 before the timer expires. In this case the timer is disabled and is not taken into account.

Note that when the device 10 is in the MRI stand-by state (block 108), the device 10 switches to the protected modified magnet mode either by the automatic detection of a relatively high ambient magnetic field prevailing in the MRI examination room as described above, or by application of a permanent magnet by an operator on the patient's chest in the region of the device (132).

The MRI stand-by state is maintained while the magnetic field sensor 20 detects a static field (test 110, CCM='false'). If, however, (i) the sensor 20 detects the presence of a magnetic field (test 110, CCM='true') and (ii) the countdown timer has not expired (test 112), the device 10 considers that the patient will be subjected soon to a strong magnetic field.

One skilled in the art will appreciate that the present invention may be practiced by other than the embodiments disclosed herein, which are provided for purposes of illustration and not of limitation.

The invention claimed is:

1. An active implantable medical device for cardiac pacing, resynchronization and/or defibrillation, comprising:
   an electronic circuit configured to provide electrical stimulation signals at a stimulation frequency; and
   a magnetic field sensor configured to detect the presence of a magnet, wherein the magnetic field sensor is configured to detect the presence of the magnet by comparing a level of a first magnetic field detected by the magnetic field sensor to a threshold magnetic field level;
   wherein the electronic circuit and magnetic field sensor are configured to provide switching between at least four different modes of operation of the active implantable medical device, wherein the electronic circuit is configured to:
      switch from a first mode of the at least four modes to a second mode of the at least four modes in response to the magnetic field sensor detecting the presence of the magnet when the active implantable medical device is in the first mode, the second mode being a non-magnetic resonance imaging (MRI) safe mode; and
      switch from a third mode of the at least four modes to a fourth mode of the at least four modes in response to the magnetic field sensor detecting the presence of the magnet when the active implantable medical device is in the third mode, the fourth mode being an MRI safe mode.

2. The device of claim 1, wherein the second mode is configured to protect the active implantable medical device from effects of a magnetic field generated by the MM equipment during the MM examination, and wherein, in the fourth mode, the electronic circuit adjusts the stimulation frequency based on a level of consumption of a power supply battery.

3. The device of claim 1, further comprising:
   transmitter/receiver telemetry providing communication coupling of the device with an external programmer device, wherein the electronic circuit is configured to receive a command to temporarily place the device in the first mode via the transmitter/receiver telemetry.

4. The device of claim 1, further comprising:
   a timer for counting a predetermined time period from a moment when the device is placed in the first mode,
   wherein the electronic circuit is configured to automatically place the device in third mode at the expiry of the timer.

5. The device of claim 4, further comprising:
   transmitter/receiver telemetry providing communication coupling of the device with an external programmer device, wherein the predetermined time period of the timer is programmable by said external programmer device and transmitted to the device via the transmitter/receiver telemetry.

6. The device of claim 1, further comprising:
   transmitter/receiver telemetry providing communication coupling of the device with an external programmer device, wherein the electronic circuit is configured to receive a command to switch the device from the first mode to the third mode via the transmitter/receiver telemetry.

7. The device of claim 1, wherein the electronic circuit is configured to inhibit switching of the device from the second mode to the first mode during a predetermined period after the switching of the device into the second mode.

8. The device of claim 7, further comprising:
transmitter/receiver telemetry providing communication coupling of the device with an external programmer device, wherein said predetermined period is programmable by said external programmer device and transmitted to the device via the transmitter/receiver telemetry.

9. The device of claim 1, wherein, in the second mode, the electronic circuit is configured to:
inhibit detection of cardiac signals;
inhibit elements of the device sensitive to deleterious effects of exposure to static and alternating radio frequency magnetic fields emitted by MM equipment; and
generate pacing pulses at a predetermined frequency, independent of the level of a battery of the device.

10. An active implantable medical device configured to perform at least one of cardiac pacing, resynchronization, or defibrillation, the active implantable medical device comprising:
a power supply battery configured to provide power to the active implantable medical device;
an electronic circuit configured to provide electrical stimulation signals at a stimulation frequency; and
a magnetic field sensor configured to measure a strength of a first magnetic field detected by the magnetic field sensor;
wherein at least one of the electronic circuit or the magnetic field sensor are configured to detect a presence of a magnet by comparing the strength of the first magnetic field detected by the magnetic field sensor to a threshold magnetic field level; and
wherein the electronic circuit and magnetic field sensor are configured to provide switching between at least four different modes of operation of the active implantable medical device by:
switching from a first mode of the at least four modes to a second mode of the at least four modes in response to the magnetic field sensor detecting the presence of the magnet when the active implantable medical device is in the first mode, the second mode being a non-magnetic resonance imaging (MRI) safe mode; and
switching from a third mode of the at least four modes to a fourth mode of the at least four modes in response to the magnetic field sensor detecting the presence of the magnet when the active implantable medical device is in the third mode, the fourth mode being an MRI safe mode.

11. The device of claim 10, wherein the second mode is configured to protect the active implantable medical device from effects of a magnetic field generated by the MM equipment during the MM examination, and wherein, in the fourth mode, the electronic circuit adjusts the stimulation frequency based on a level of consumption of a power supply battery.

12. The device of claim 10, wherein the magnet is a separate device from non-operating MRI equipment.

13. The device of claim 10, wherein the threshold magnetic field level is 1 mT.

14. The device of claim 10, wherein the first magnetic field detected by the magnetic field sensor comprises a static magnetic field, and wherein the magnetic field generated by the MRI equipment during the MM examination comprises both a static magnetic field and an alternating magnetic field.

15. The device of claim 10, wherein the magnetic field sensor is configured to detect an absence of the first magnetic field after detecting presence of the first magnetic field, and wherein the electronic circuit is configured to switch the active implantable medical device from the second mode to the third mode in response to the magnetic field sensor detecting the absence of the first magnetic field.

16. The device of claim 10, wherein the magnet is a permanent magnet that emits a magnetic field and wherein the magnetic field sensor is configured to detect the magnetic field emitted by the permanent magnet.

17. A method comprising:
measuring a strength of a first magnetic field detected by a magnetic field sensor of an active implantable medical device;
detecting a presence of a magnet by comparing a level of the first magnetic field detected by the magnetic field sensor to a threshold magnetic field level;
switching between at least four different modes of operation of the active implantable medical device, wherein the electronic circuit is configured to switch between the at least four modes of operation by:
switching the active implantable medical device from a first mode of the at least four modes to a second mode of the at least four modes in response to detecting the presence of the magnet when the active implantable medical device is in the first mode, the second mode being a non-magnetic resonance imaging (MM) safe mode; and
switching the active implantable medical device from a third mode of the at least four modes to a fourth mode of the at least four modes in response to detecting the presence of the magnet when the active implantable medical device is in the third mode, the fourth mode being an Mill safe mode.

18. The method of claim 17, further comprising:
protecting the active implantable medical device from effects of a magnetic field generated by the MM equipment during the MM examination when the active implantable medical device is in the second mode; and
adjusting the stimulation frequency based on a level of consumption of the power supply battery when the active implantable medical device is in the fourth mode.

* * * * *